United States Patent [19]

Dreikorn

[11] 4,152,460

[45] May 1, 1979

[54] 3-CHLORO-2,6-DINITRO-N-(SUBSTITUTED PHENYL)-4-(TRIFLUOROMETHYL)BENZENAMINES

[75] Inventor: Barry A. Dreikorn, Indianapolis, Ind.

[73] Assignee: Eli Lilly and Company, Indianapolis, Ind.

[21] Appl. No.: 873,190

[22] Filed: Jan. 30, 1978

[51] Int. Cl.$^2$ ............... A61K 31/04; A61K 31/275; C07C 87/60; C07C 121/78
[52] U.S. Cl. .......................... 424/330; 260/465 E; 260/576; 424/304
[58] Field of Search ............... 260/465 E, 576; 424/304, 330

[56] References Cited

U.S. PATENT DOCUMENTS

| 3,764,624 | 10/1973 | Strong et al. | 260/576 X |
| 3,950,377 | 4/1976 | Bartow | 260/465 E |

*Primary Examiner*—Dolph H. Torrence
*Attorney, Agent, or Firm*—Dwight E. Morrison; Arthur R. Whale

[57] ABSTRACT

A new class of substituted 2,6-dinitrobenzenamines bearing a chlorine atom in the 3-position, active against a number of plant pathogenic fungi, as well as methods for the use of the compounds and fungicidal compositions containing the compounds.

22 Claims, No Drawings

3-CHLORO-2,6-DINITRO-N-(SUBSTITUTED PHENYL)-4-(TRIFLUOROMETHYL)BENZENAMINES

BACKGROUND OF THE INVENTION

1. Field of the Invention

This invention relates to a new class of substituted 2,6-dinitrobenzenamines. More particularly, this invention relates to substituted 2,6-dinitrobenzenamines having a chlorine atom in the 3-position.

2. Description of the Prior Art

In the prior art Barlow, U.S. Pat. No. 3,950,377 (Apr. 13, 1976), discloses and claims a group of 4-cyano- or 4-trifluoromethyl-2,6-dinitrodiphenylamine derivatives alleged to be toxic to a wide variety of insect and other invertebrate pests. In addition, this patent alleges the compounds and compositions disclosed therein are also useful in the control of fungal pests of plants.

SUMMARY OF THE INVENTION

This invention relates to a new class of substituted 2,6-dinitrobenzenamines bearing a chlorine atom in the 3-position, as well as to compositions containing the novel compounds and methods for controlling plant pathogenic fungi utilizing the novel compounds and compositions thereof.

DESCRIPTION OF THE PREFERRED EMBODIMENT

This invention relates to a new class of substituted 2,6-dinitrobenzenamines of the formula:

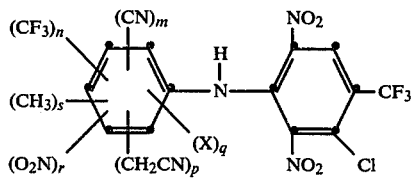

wherein
X is chloro, fluoro, or bromo;
m, p, and s are individually 0 or 1;
n is 0, 1 or 2;
q and r are individually 0, 1, 2, or 3;
the sum of m, n, p, q, r, and s is 1 to 3;
with the proviso that when n is 2, then m, p, q, r, and s are all 0, and the trifluoromethyl groups must be in the 3- and 5-positions; with the further proviso that when s is 1, m and p both are 0, and the sum of n, q, and r is not 0; and with the further proviso that q is 1 only when the sum of m, n, r, and s is not 0.

This invention also relates to compositions for controlling plant pathogenic fungi comprising a fungicidally-effective amount of a compound of the above structural formula, an inert diluent, and a surfactant.

In addition, this invention also relates to a method for controlling plant pathogenic fungi which comprises applying to the loci of the fungi a fungicidally-effective amount of a compound coming within the scope of the above generic formula.

The novel compounds of this invention bear a chlorine atom in the 3-position and are prepared from 2,4-dichloro-3,5-dinitrobenzotrifluoride, the preparation of which compound is described in U.S. Pat. No. 3,617,252.

The novel compounds of this invention can be readily prepared following a number of different procedures. In one procedure, a substituted or unsubstituted aniline is allowed to react with a base, such as sodium hydride, in a suitable solvent, such as dimethylformamide, at a temperature of from about −15° to about −50° C. Other suitable bases for use in the reaction include sodium amide, and potassium amide. Other suitable solvents include dimethylsulfoxide. The reaction mixture is allowed to warm to about room temperature. The reaction mixture is then cooled to from about 0° to about −40° C., and a solution of the 2,4-dichloro-3,5-dinitrobenzotrifluoride in an inert solvent such as dimethylformamide is added. The reaction mixture is stirred and allowed to warm to room temperature overnight, then diluted with ice water. The solid which forms is stirred for several hours, collected by filtration, and purified by recrystallization.

In a second method of preparation, the substituted aniline and the 2,4-dichloro-3,5-dinitrobenzotrifluoride are mixed in a suitable solvent such as ethanol and refluxed for a period of time sufficient to complete the reaction. Other suitable solvents include propanol and butanol. An excess of the substituted aniline can be used as the acid scavenger in the reaction. Other suitable acid scavengers include triethylamine, sodium carbonate and potassium carbonate. The time for refluxing varies with the reactants and solvents and is from about 4 hours to as much as 48 hours, with the temperature varying from about 80° C. to about 120° C. At the end of the heating period, the reaction mixture is cooled and the solids which separate are collected, dried, and recrystallized from a suitable solvent to give the desired product.

In yet another preparative method, the substituted aniline is allowed to react with the 2,4-dichloro-3,5-dinitrobenzotrifluoride in the presence of an acid scavenger such as anhydrous sodium carbonate, in a suitable solvent, such as dimethylformamide, at a reaction temperature varying from about room temperature to the temperature of a steam bath for a period of from about 12 hours to as much as 96 hours or more, as may be required to complete the reaction. The reaction may also be carried out using an excess of the substituted aniline as the acid scavenger. Other suitable acid scavengers include potassium carbonate and triethylamine. Other suitable solvents include dimethyl sulfoxide. At the end of the reaction time, the reaction mixture is diluted with water, made acid with dilute acid, and the acidic mixture extracted with a suitable solvent such as methylene dichloride. The methylene dichloride solution is dried, the solvent evaporated and the residue taken up in more methylene dichloride and chromatographed over a silica gel column. The fractions from the column are combined, concentrated in vacuo, and the residue recrystallized from a suitable solvent such as ethanol to give the desired product. The reaction can also be run with solvents such as benzene or toluene, and in such cases, the reaction mixture is extracted with acid to remove the unreacted aniline, the benzene or toluene solution dried, the solvent evaporated, and the residue worked up as previously described by chromatographing over a silica gel column.

The intermediate anilines are all commercially available compounds, or are known in the prior art.

The preparation of the novel compounds of this invention is further illustrated by the following examples.

EXAMPLE 1

3-Chloro-2,6-dinitro-4-(trifluoromethyl)-N-[2-(trifluoromethyl)phenyl]benzenamine A 3.2 g. portion of sodium hydride (50%) was washed with hexane, the hexane decanted, and replaced with 50 ml. of dimethylformamide. The suspension thereby obtained was cooled to about −50° C. and there was added thereto a solution prepared from 10.4 g. (0.065 moles) of 2-aminobenzotrifluoride and 35 ml. of dimethylformamide. The resulting mixture was allowed to warm to ambient room temperature, then cooled to about −30° C. and there was added thereto 20 g. of 2,4-dichloro-3,5-dinitrobenzotrifluoride and the resulting reaction mixture was allowed to warm to ambient room temperature overnight. The reaction mixture was poured into 4 liters of ice water and the aqueous mixture stirred for about 2 hours. The mixture was filtered and the solid which was collected was recrystallized from a mixture of ethanol and water to yield product having a melting point of about 135°–137° C., and identified as 3-chloro-2,6-dinitro-4-(trifluoromethyl)-N-[2-(trifluoromethyl)phenyl]benzenamine. Yield 8.8 g.

| Analyses calculated for: $C_{14}H_6ClF_6N_3O_4$: | | |
|---|---|---|
| | Theoretical | Found |
| C | 39.14 | 39.02 |
| H | 1.41 | 1.38 |
| N | 9.78 | 9.83 |

Following the same general procedure set forth in Example 1, additional compounds were prepared and identified. The compounds, together with the principal starting materials and weights thereof used in the syntheses, are listed in the examples set forth hereinafter.

EXAMPLE 2

3-Chloro-N-(3,5-dichlorophenyl)-2,6-dinitro-4-(trifluoromethyl)benzenamine, having a melting point of about 138°–139° C., and weighing 11.6 g., from 10.6 g. of 3,5-dichloroaniline and 20 g. of 2,4-dichloro-3,5-dinitrobenzotrifluoride.

| Analyses calculated for $C_{13}H_5Cl_3F_3N_3O_4$: | | |
|---|---|---|
| | Theoretical | Found |
| C | 36.27 | 36.53 |
| H | 1.17 | 1.24 |
| N | 9.76 | 9.85 |

EXAMPLE 3

3-Chloro-2,6-dinitro-4-(trifluoromethyl)-N-[2-(cyano)phenyl]benzenamine, having a melting point of about 112°–113° C., and weighing 5.3 g., from 7.7 g. of 2-aminobenzonitrile, and 20 g. of 2,4-dichloro-3,5-dinitrobenzotrifluoride.

| Analyses calculated for $C_{14}H_6ClF_3N_4O_4$: | | |
|---|---|---|
| | Theoretical | Found |
| C | 43.49 | 43.26 |
| H | 1.56 | 1.59 |
| N | 14.49 | 14.46 |

EXAMPLE 4

3-Chloro-2,6-dinitro-4-(trifluoromethyl)-N-(2,4,6-trichlorophenyl)benzenamine, having a melting point of about 140°–141° C., and weighing 15.4 g., from 20 g. of 2,4,6-trichloroaniline and 30 g. of 2,4-dichloro-3,5-dinitrobenzotrifluoride.

| Analyses calculated for $C_{13}H_4Cl_4F_3N_3O_4$: | | |
|---|---|---|
| | Theoretical | Found |
| C | 33.58 | 33.80 |
| H | 0.87 | 0.77 |
| N | 9.04 | 9.27 |
| Cl | 30.50 | 30.30 |

EXAMPLE 5

3-Chloro-N-(2,4-dichlorophenyl)-2,6-dinitro-4-(trifluoromethyl)benzenamine, having a melting point of about 106°–108° C., and weighing 5.0 g., from 10.6 g. (0.065 mole) of 2,4-dichloroaniline and 20 g. of 2,4-dichloro-3,5-dinitrobenzotrifluoride.

| Analyses calculated for $C_{13}H_5Cl_3F_3N_3O_4$: | | |
|---|---|---|
| | Theoretical | Found |
| C | 36.27 | 36.46 |
| H | 1.17 | 1.14 |
| N | 9.76 | 9.81 |

EXAMPLE 6

3-Chloro-N-(2,5-dichlorophenyl)-2,6-dinitro-4-(trifluoromethyl)benzenamine, having a melting point of about 163°–165° C., and weighing 4.35 g., from 10.6 g. of 2,5-dichloroaniline and 20 g. of 2,4-dichloro-3,5-dinitrobenzotrifluoride.

| Analyses calculated for $C_{13}H_5Cl_3F_3N_3O_4$: | | |
|---|---|---|
| | Theoretical | Found |
| C | 36.27 | 36.42 |
| H | 1.17 | 1.00 |
| N | 9.76 | 9.90 |

EXAMPLE 7

3-Chloro-N-(2,6-dichlorophenyl)-2,6-dinitro-4-(trifluoromethyl)benzenamine, having a melting point of about 151°–152° C., and weighing 12.2 g., from 10.6 g. of 2,6-dichloroaniline and 20 g. of 2,4-dichloro-3,5-dinitrobenzotrifluoride.

| Analyses calculated for $C_{13}H_5Cl_3F_3N_3O_4$: | | |
|---|---|---|
| | Theoretical | Found |
| C | 36.27 | 36.42 |
| H | 1.17 | 1.15 |
| N | 9.76 | 9.75 |

EXAMPLE 8

3-Chloro-N-(2,5-dibromophenyl)-2,6-dinitro-4-(trifluoromethyl)benzenamine, having a melting point of about 176°–177° C., and weighing 2.5 g., from 16.3 g. of 2,5-bromoaniline and 20 g. of 2,4-dichloro-3,5-dinitrobenzotrifluoride.

| Analyses calculated for $C_{13}H_5ClBr_2F_3N_3O_4$: | | |
|---|---|---|
| | Theoretical | Found |
| C | 30.06 | 30.24 |
| H | 0.97 | 0.78 |

-continued

| Analyses calculated for $C_{13}H_5ClBr_2F_3N_3O_4$: | | |
|---|---|---|
| | Theoretical | Found |
| N | 8.09 | 7.83 |

EXAMPLE 9

3-Chloro-N-(2,6-dibromophenyl)-2,6-dinitro-4-(trifluoromethyl)benzenamine, having a melting point of about 164°–165° C., and weighing 14.6 g., from 16.3 g. of 2,6-dibromoaniline and 20 g. of 2,4-dichloro-3,5-dinitrobenzotrifluoride.

| Analyses calculated for $C_{13}H_5Br_2ClF_3N_3O_4$: | | |
|---|---|---|
| | Theoretical | Found |
| C | 30.06 | 30.11 |
| H | 0.97 | 0.96 |
| N | 8.09 | 8.11 |

EXAMPLE 10

3-Chloro-N-(2,4-dibromophenyl)-2,6-dinitro-4-(trifluoromethyl)benzenamine, having a melting point of about 122°–123° C., and weighing 5.5 g., from 16.3 g. of 2,4-dibromoaniline and 20 g. of 2,4-dichloro-3,5-dinitrobenzotrifluoride.

| Analyses calculated for $C_{13}H_5Br_2ClF_3N_3O_4$: | | |
|---|---|---|
| | Theoretical | Found |
| C | 30.06 | 30.07 |
| H | 0.97 | 1.10 |
| N | 8.09 | 8.24 |

EXAMPLE 11

3-Chloro-2,6-dinitro-N-(2,4,5-trichlorophenyl)-4-(trifluoromethyl)benzenamine, having a melting point of about 144°–145° C., and weighing 10.5 g., from 12.8 g. of 2,4,5-trichloroaniline and 20 g. of 2,4-dichloro-3,5-dinitrobenzotrifluoride.

| Analyses calculated for $C_{13}H_4Cl_4F_3N_3O_4$: | | |
|---|---|---|
| | Theoretical | Found |
| C | 33.58 | 33.87 |
| H | 0.87 | 1.17 |
| N | 9.04 | 8.97 |

EXAMPLE 12

3-Chloro-2,6-dinitro-N-(3,4,5-trichlorophenyl)-4-(trifluoromethyl)benzenamine, having a melting point of about 186°–187° C., and weighing 12.6 g., from 12.8 g. of 3,4,5-trichloroaniline and 20 g. of 2,4-dichloro-3,5-dinitrobenzotrifluoride.

| Analyses calculated for $C_{13}H_4Cl_4F_3N_3O_4$: | | |
|---|---|---|
| | Theoretical | Found |
| C | 33.58 | 33.86 |
| H | 0.87 | 0.97 |
| N | 9.04 | 9.21 |

EXAMPLE 13

3-Chloro-2,6-dinitro-N-(2-nitrophenyl)-4-(trifluoromethyl)benzenamine, having a melting point of about 136°–137° C., and weighing 7.05 g., from 9 g. of 2-nitroaniline and 20 g. of 2,4-dichloro-3,5-dinitrobenzotrifluoride.

| Analyses calculated for $C_{13}H_6ClF_3N_4O_6$: | | |
|---|---|---|
| | Theoretical | Found |
| C | 38.40 | 38.66 |
| H | 1.49 | 1.47 |
| N | 13.78 | 13.67 |

EXAMPLE 14

3-Chloro-2,6-dinitro-N-phenyl-4-(trifluoromethyl)benzenamine, having a melting point of about 128°–130° C., and weighing 2.5 g., from 15.25 g. of aniline and 50 g. of 2,4-dichloro-3,5-dinitrobenzotrifluoride.

| Analyses calculated for $C_{13}H_7ClF_3N_3O_4$: | | |
|---|---|---|
| | Theoretical | Found |
| C | 43.17 | 43.41 |
| H | 1.95 | 2.16 |
| N | 11.62 | 11.41 |

EXAMPLE 15

3-Chloro-N-(2-chloro-4-nitrophenyl)-2,6-dinitro-4-(trifluoromethyl)benzenamine, having a melting point of about 141°–142° C., from 11.2 g. of 2-chloro-4-nitroaniline and 20 g. of 2,4-dichloro-3,5-dinitrobenzotrifluoride.

| Analyses calculated for $C_{13}H_5Cl_2F_3N_4O_6$: | | |
|---|---|---|
| | Theoretical | Found |
| C | 35.40 | 35.43 |
| H | 1.14 | 1.13 |
| N | 12.70 | 12.43 |

EXAMPLE 16

N-(2-Bromo-4-nitrophenyl)-3-chloro-2,6-dinitro-4-(trifluoromethyl)benzenamine, having a melting point of about 144°–145° C., and weighing 6.5 g., from 14.1 g. of 2-bromo-4-nitroaniline and 20 g. of 2,4-dichloro-3,5-dinitrobenzotrifluoride.

| Analyses calculated for $C_{13}H_5BrClF_3N_4O_6$: | | |
|---|---|---|
| | Theoretical | Found |
| C | 32.16 | 32.25 |
| H | 1.04 | 1.27 |
| N | 11.54 | 11.70 |

EXAMPLE 17

3-Chloro-N-(2,6-dichloro-4-nitrophenyl)-2,6-dinitro-4-(trifluoromethyl)benzenamine, having a melting point of about 176°–177° C., and weighing 5.9 g., from 13.45 g. of 2,6-dichloro-4-nitroaniline and 20 g. of 2,4-dichloro-3,5-dinitrobenzotrifluoride.

| Analyses calculated for $C_{13}H_4Cl_3F_3N_4O_6$: | | |
|---|---|---|
| | Theoretical | Found |
| C | 32.83 | 33.05 |
| H | 0.85 | 1.02 |
| N | 11.78 | 12.04 |

EXAMPLE 18

3-Chloro-N-(2,4-difluorophenyl)-2,6-dinitro-4-(trifluoromethyl)benzenamine, having a melting point of about 111°–112° C., and weighing 6.8 g., from 8.4 g. of 2,4-difluoroaniline and 20 g. of 2,4-dichloro-3,5-dinitrobenzotrifluoride.

| Analyses calculated for $C_{13}H_5ClF_5N_3O_4$: | | |
|---|---|---|
| | Theoretical | Found |
| C | 39.25 | 39.53 |
| H | 1.26 | 1.54 |
| N | 10.56 | 10.41 |

EXAMPLE 19

3-Chloro-N-(3,4-dichlorophenyl)-2,6-dinitro-4-(trifluoromethyl)benzenamine

A solution of 21.2 g. (0.130 mole) of 3,4-dichloroaniline and 20 g. (0.065 mole) of 2,4-dichloro-3,5-dinitrobenzotrifluoride in 250 ml. of ethanol was refluxed for about 4 days. The reaction mixture was cooled and the solid which separated on cooling was filtered off and dried. The solid was recrystallized from ethanol to yield material having a melting point of about 152°–153° C., and identified as 3-chloro-N-(3,4-dichlorophenyl)-2,6-dinitro-4-(trifluoromethyl)benzenamine.

| Analyses calculated for $C_{13}H_5Cl_3F_3N_3O_4$: | | |
|---|---|---|
| | Theoretical | Found |
| C | 36.27 | 36.35 |
| H | 1.17 | 1.33 |
| N | 9.76 | 9.91 |

Following the same general procedure set forth in Example 19, additional compounds were prepared and identified. The compounds, together with the principal starting materials and weights thereof used in the syntheses, are listed in the examples set forth hereinafter.

EXAMPLE 20

3-Chloro-2,6-dinitro-N-(4-nitrophenyl)-4-(trifluoromethyl)benzenamine, having a melting point of about 207°–208° C., and weighing 12 g., from 18 g. of 4-nitroaniline and 20 g. of 2,4-dichloro-3,5-dinitrobenzotrifluoride.

| Analyses calculated for $C_{13}H_6ClF_3N_4O_6$: | | |
|---|---|---|
| | Theoretical | Found |
| C | 38.40 | 38.66 |
| H | 1.49 | 1.67 |
| N | 13.78 | 13.88 |

EXAMPLE 21

3-Chloro-N-(3,4-dibromophenyl)-2,6-dinitro-4-(trifluoromethyl)benzenamine, having a melting point of about 166°–167° C., weighing 2.4 g., from 5 g. of 3,4-dibromoaniline and 3 g. of 2,4-dichloro-3,5-dinitrobenzotrifluoride.

| Analyses calculated for $C_{13}H_5Br_2ClF_3N_3O_4$: | | |
|---|---|---|
| | Theoretical | Found |
| C | 30.03 | 30.25 |
| H | 0.97 | 1.09 |
| N | 8.09 | 8.06 |

EXAMPLE 22

3-Chloro-2,6-dinitro-4-(trifluoromethyl)-N-[4-(trifluoromethyl)phenyl]benzenamine, having a melting point of about 154°–155° C., and weighing 8.25 g., from 12 g. of 4-aminobenzotrifluoride and 11.35 g. of 2,4-dichloro-3,5-dinitrobenzotrifluoride.

| Analyses calculated for $C_{14}H_6ClF_6N_3O_4$: | | |
|---|---|---|
| | Theoretical | Found |
| C | 39.14 | 39.37 |
| H | 1.41 | 1.55 |
| N | 9.78 | 9.90 |

EXAMPLE 23

3-Chloro-2,6-dinitro-4-(trifluoromethyl)-N-[3-(trifluoromethyl)phenyl]benzenamine, having a melting point of about 159°–160° C., and weighing 8 g., from 12.0 g. of 3-aminobenzotrifluoride and 11.35 g. of 2,4-dichloro-3,5-dinitrobenzotrifluoride.

| Analyses calculated for $C_{14}H_6ClF_6N_3O_4$: | | |
|---|---|---|
| | Theoretical | Found |
| C | 39.14 | 39.04 |
| H | 1.14 | 1.36 |
| N | 9.78 | 9.77 |

EXAMPLE 24

3-Chloro-N-[4-(cyanomethyl)phenyl]-2,6-dinitro-4-(trifluoromethyl)benzenamine, having a melting point of about 173°–174° C., and weighing 13.0 g., from 13.2 g. of 4-cyanomethylaniline and 15.25 g. of 2,4-dichloro-3,5-dinitrobenzotrifluoride.

| Analyses calculated for $C_{15}H_8ClF_3N_4O_4$: | | |
|---|---|---|
| | Theoretical | Found |
| C | 44.96 | 45.18 |
| H | 2.01 | 2.17 |
| N | 13.98 | 14.14 |

EXAMPLE 25

N-(2-Bromo-4-methylphenyl)-3-chloro-2,6-dinitro-4-(trifluoromethyl)benzenamine, having a melting point of about 119°–120° C., and weighing 5.0 g., from 9.3 g. of 2-bromo-4-toluidine and 7.6 g. of 2,4-dichloro-3,5-dinitrobenzotrifluoride.

| Analyses calculated for $C_{14}H_8BrClF_3N_3O_4$: | | |
|---|---|---|
| | Theoretical | Found |
| C | 36.99 | 37.24 |
| H | 1.77 | 2.05 |
| N | 9.24 | 9.54 |

EXAMPLE 26

3-Chloro-N-(3-cyanophenyl)-2,6-dinitro-4-(trifluoromethyl)benzenamine, having a melting point of about 147°-149° C., and weighing 4.3 g., from 4.72 g. of 3-aminobenzonitrile and 6.1 g. of 2,4-dichloro-3,5-dinitrobenzotrifluoride.

| Analyses calculated for $C_{14}H_6ClF_3N_4O_4$: | | |
|---|---|---|
| | Theoretical | Found |
| C | 43.49 | 43.71 |
| H | 1.56 | 1.77 |
| N | 14.49 | 14.46 |

EXAMPLE 27

3-Chloro-N-(4-cyanophenyl)-2,6-dinitro-4-(trifluoromethyl)benzenamine, having a melting point of about 179°-181° C., from 2.36 g. of 4-cyanoaniline and 3.0 g. of 2,4-dichloro-3,5-dinitrobenzotrifluoride.

| Analyses calculated for $C_{14}H_6ClF_3N_3O_4$: | | |
|---|---|---|
| | Theoretical | Found |
| C | 43.49 | 43.37 |
| H | 1.56 | 1.81 |
| N | 14.49 | 14.17 |

EXAMPLE 28

3-Chloro-N-[4-chloro-3-(trifluoromethyl)phenyl]-2,6-dinitro-4-(trifluoromethyl)benzenamine, having a melting point of about 169°-170° C., and weighing 16.45 g., from 25 g. of 5-amino-2-chlorobenzotrifluoride and 19.5 g. of 2,4-dichloro-3,5-dinitrobenzotrifluoride.

| Analyses calculated for $C_{14}H_5Cl_2F_6N_3O_4$: | | |
|---|---|---|
| | Theoretical | Found |
| C | 36.23 | 35.95 |
| H | 1.09 | 1.02 |
| N | 9.05 | 9.24 |

EXAMPLE 29

3-Chloro-2,6-dinitro-N-(3,5-dinitrophenyl)-4-(trifluoromethyl)benzenamine

A mixture of 1.83 g. (0.01 mole) of 3,5-dinitroaniline, 3.05 g. (0.01 mole) of 2,4-dichloro-3,5-dinitrobenzotrifluoride, 0.53 g. of sodium carbonate, and 20 ml. of dimethylformamide was heated on a steam bath for about 4 days. At the end of that time additional sodium carbonate was added to the reaction mixture and heating was continued for 2 days. The reaction product mixture was worked up by pouring it into water and acidifying the mixture with dilute aqueous acid and extracting with methylene dichloride. The methylene dichloride layer was dried, the drying agent filtered off and the filtrate concentrated in vacuo. The residue was taken up in methylene dichloride and chromatographed over silica gel. The fractions were combined and evaporated and the residue recrystallized from ethanol to give product having a melting point of about 188°-189° C., and identified as 3-chloro-2,6-dinitro-N-(3,5-dinitrophenyl)-4-(trifluoromethyl)benzenamine. Yield 0.65 g.

| Analyses calculated for $C_{13}H_5ClF_3N_5O_8$: | | |
|---|---|---|
| | Theoretical | Found |
| C | 34.57 | 34.83 |
| H | 1.12 | 1.22 |
| N | 15.51 | 15.74 |

Following the same general procedure set forth in Example 29, an additional compound was prepared and identified. The compound, together with the principal starting materials and weights thereof used in the synthesis, is listed in the example set forth hereinafter.

EXAMPLE 30

N-(2-Bromo-4,6-dinitrophenyl)-3-chloro-2,6-dinitro-4-(trifluoromethyl)benzenamine, having a melting point of about 144°-146° C., and weighing 1.3 g., from 5.24 g. of 2-bromo-4,6-dinitroaniline and 6.10 g. of 2,4-dichloro-3,5-dinitrobenzotrifluoride.

| Analyses calculated for $C_{13}H_4BrClF_3N_5O_8$: | | |
|---|---|---|
| | Theoretical | Found |
| C | 29.43 | 29.68 |
| H | 0.76 | 0.97 |
| N | 13.20 | 13.05 |

EXAMPLE 31

N-[3,5-bis(trifluoromethyl)phenyl]-3-chloro-2,6-dinitro-4-(trifluoromethyl)benzenamine A mixture of 15.0 g. (0.066 mole) of 3,5-bis-(trifluoromethyl)aniline, 100 ml. of n-butanol, 20.0 g. (0.066 mole) of 2,4-dichloro-3,5-dinitrobenzotrifluoride, and 11 ml. of triethylamine was prepared in a 250 ml. flask and the mixture was refluxed for about 48 hours. The reaction mixture was allowed to cool and the solvent removed in vacuo. The residue was crystallized by chromatographing it on a silica gel column using toluene as the eluant. The fractions were concentrated in vacuo and the combined residue recrystallized from ethanol. There was obtained product having a melting point of about 156°-158° C. It was identified as N-[3,5-bis(trifluoromethyl)phenyl]-3-chloro-2,6-dinitro-4-(trifluoromethyl)benzenamine. Yield 3.2 g.

| Analyses calculated for $C_{15}H_5ClF_9N_3O_4$: | | |
|---|---|---|
| | Theoretical | Found |
| C | 36.20 | 36.37 |
| H | 1.01 | 0.97 |
| N | 8.44 | 8.42 |

To be utilized in the novel plant fungicidal method of the present invention, the above-described compounds may be formulated in novel compositions comprising one of the above-described compounds as the active ingredient and a carrier. Such novel compositions are useful and convenient for preparing the mixture desired for application to the loci of desired fungus control.

Each active compound may be formulated as a simple solution in an appropriate solvent in which it is completely soluble at the desired concentration. Such solvent systems include alcohols, acetone, aqueous alcohol and aqueous acetone, xylene, heavy aromatic naphthas, and other organic solvents. These simple solutions may be further modified by the addition of various surfactants, emulsifying or dispersing agents, colorants, odorants, antifoaming agents, or other fungicides which supplement or synergize the respective activity of the compound being formulated.

The compounds useful in the present embodiment of this invention may also be formulated in various types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of an active ingredient for agricultural and industrial applications of fungitoxicants. These formulations may contain as little as 0.1% or as much as 90% by weight of the active ingredient.

Dust formulations are prepared by mixing the active ingredient with finely divided solids which act as dispersants and carriers for the fungitoxicant in applying it to the locus of desired fungus control. Typical solids which may be utilized in preparing dust formulations of the active ingredient useful in the invention include talc, kieselguhr, finely divided clay, fuller's earth, or other common organic or inorganic solids. Solids utilized in preparing dust formulations of the active ingredient normally have a particle size of 50 microns or less. The active ingredient of these dust formulations is present commonly in from as little as 0.5% to as much as 90% or more by weight of the composition.

Granular formulations of the active ingredient are prepared by impregnating or adsorbing the toxicant on or into relatively coarse particles of inert solids such as sand, attapulgite clay, gypsum, corncobs, vermiculite, or other inorganic or organic solids. The active ingredient of these granular formulations is commonly present in from 0.1% to as much as 90% or more by weight of the composition.

The compounds useful in the instant embodiment of this invention may also be formulated as wettable powders. Wettable powder formulations are solid compositions of matter wherein the active ingredient is absorbed or adsorbed in or on a sorptive carrier such as finely divided clay, talc, gypsum, lime, wood flour, fuller's earth, kieselguhr or the like. These formulations preferably are made to contain 0.5% to 90% of active ingredient. These wettable powder formulations commonly contain a small amount of a wetting, dispersing, or emulsifying agent to facilitate dispersion in water or other liquid carrier utilized to distribute the fungitoxicant to the locus of desired fungus control. Suitable wetting and/or dispersing agents include condensed aryl sulfonic acids and sodium salts thereof, sodium lignosulfate, sulfonate-oxide condensate blends, alkyl aryl polyether alcohols, sulfonated nonionic blends, anionic wetting agents, and the like. Suitable emulsifying agents can be of the nonionic or ionic types, or blends thereof, and include condensation products of alkylene oxides with phenols and organic acids, polyoxyethylene derivatives of sorbitan esters, complex ether-alcohols, ionics of the aralkyl sulfonate type, and the like.

The compounds usable in this embodiment of this invention may also be formulated as emulsifiable concentrates. Emulsifiable concentrate formulations are homogenous, liquid or paste compositions containing the active ingredient, which compositions will disperse in water or other liquid carrier to facilitate application of the fungitoxicant to the locus of desired fungi control. Such emulsifiable concentrate formulations of the active ingredients may contain only the active ingredient with a liquid or solid emulsifying agent, or may contain other relatively nonvolatile organic solvents such as isophorone, dioxane, heavy aromatic naphthas, xylene, or dimethylformamide. Emulsifying agents suitable for use in preparing these emulsifiable concentrate compositions are described in the immediately previous paragraph. The active ingredient in such formulation commonly comprises from about 1% to about 70% by weight of the fungitoxicant composition.

The formulation of agricultural chemicals is a well-developed art and those skilled in the art will have no difficulty in preparing formulations of these novel benzenamine compounds for use in the practice of the instant embodiment of this invention.

The following experimental procedures were used to demonstrate the fungicidal activity of compounds coming within the scope of the generic formula of this application.

TRIAL 1

The usefulness of the compounds of this invention to reduce the incidence and severity of grape downy mildew was demonstrated in greenhouse tests. The test compounds were formulated by mixing 70 mg. of the compound with 2 ml. of a solution prepared from 500 ml. of acetone, 500 ml. of ethanol, and 100 ml. of Tween 20. (Tween 20 is a polyoxyethylene sorbitan monolaurate made by Atlas Chemical Division of ICI America, Inc., Wilmington, Del.) The sample was then diluted with 175 ml. of deionized water containing one drop of Dow Corning antifoam C emulsion per 2 l. of water. (Dow Corning antifoam C is a silicone complex antifoaming agent made by Dow Corning Corporation, Midland, Mich.) The final formulation contained 400 ppm. of the test compound, 10,000 ppm. of organic solvents, and 1,000 ppm. of Tween 20. This solution was diluted with deionized water to obtain the lower concentration of the particular test compound.

On the day the test was started, young expanding leaves were detached from grape vines grown in the greenhouse. One leaf was placed bottom side up in a plastic petri plate containing a Whatman filter paper placed on top of an expanded plastic mat to keep the leaf above the water flooding the bottom of the petri plate. A water-soaked wad of cotton was wrapped around the petriole base of the leaf. The test chemical at the desired concentration was sprayed on the underside of the leaf to run off and the leaf allowed to dry. As soon as the leaf dried, it was inoculated by spraying with a conidial suspension of *Plasmopara viticola* using a DeVilbiss sprayer. The conidial suspension was prepared as follows. Conidia were obtained from recently infected leaf tissue stored in the chill room at 5° C. The conidia were washed off the leaf's surface with a brush and suspended in deionized water to obtain the inoculation suspension.

After inoculation the plates were placed in a moist chamber. Cool white fluorescent lamps above the moist chamber hood provided 200 to 400 foot-candles of light to the leaves on a cycle of 14 hours of light and 10 hours of darkness at 68° F. The leaves were observed for disease symptoms and the results were recorded seven days after treatment. A rating scale of 1 to 5 was used to record the results, in which scale 1 equals severe disease (or no control), 2 equals moderate dsease, 3 equals slight disease, 4 equals very slight disease, and 5 equals no disease (or 100% control).

The results of testing representative compounds of this invention are reported in Table 1. In the table, column 1 identifies the test compounds by operating example number; column 2, the application rate in parts per million (ppm); and column 3, the disease control ratings at the indicated ppm. application rates.

Table 1

| Compound of Example No. | Appln. Rate ppm | Grape Downy Mildew Control Rating |
|---|---|---|
| 1 | 400 | 5 |
|  | 100 | 5 |
|  | 25 | 4 |
|  | 6 | 3 |
| 2 | 400 | 5 |
|  | 100 | 5 |
|  | 25 | 4 |
| 3 | 400 | 5 |
|  | 100 | 5 |
|  | 25 | 3.5 |
|  | 6 | 3 |
| 4 | 400 | 5 |
|  | 100 | 5 |
|  | 25 | 5 |
|  | 6 | 5 |
| 5 | 400 | 5 |
|  | 100 | 4.5 |
|  | 25 | 2.5 |
| 6 | 400 | 4 |
| 10 | 400 | 5 |
|  | 100 | 4 |
| 11 | 400 | 5 |
|  | 100 | 5 |
|  | 25 | 4.5 |
|  | 6 | 3 |
| 12 | 400 | 5 |
|  | 100 | 5 |
|  | 25 | 4 |
|  | 6 | 3 |
| 13 | 400 | 5 |
|  | 100 | 4.5 |
|  | 25 | 4.5 |
| 14 | 400 | 3.5 |
|  | 100 | 3 |
| 15 | 400 | 5 |
|  | 100 | 5 |
|  | 25 | 5 |
|  | 6 | 5 |
| 16 | 400 | 5 |
|  | 100 | 5 |
|  | 25 | 5 |
|  | 6 | 5 |
| 17 | 400 | 5 |
| 19 | 400 | 4.5 |
|  | 100 | 4 |
|  | 25 | 3 |
| 20 | 400 | 5 |
|  | 100 | 5 |
|  | 25 | 4.5 |
|  | 6 | 4 |
| 22 | 400 | 5 |
|  | 100 | 5 |
|  | 25 | 4 |
| 24 | 400 | 3 |
| 25 | 400 | 3 |
| 26 | 400 | 3 |
| 28 | 400 | 3 |
|  | 100 | 4.5 |
|  | 25 | 4.5 |
|  | 6 | 5 |

TRIAL 2

The compounds were tested against *Colletotrichum lagenarium*, the causative organism of cucumber anthracnose. Formulation of the test compounds was done as described in Trial 1. Three cucumber seeds were planted in 7.5 cm. square plastic pots, and after germination the plants were thinned to two per pot. On the 15th day after planting, the test chemical was sprayed on all leaf surfaces and allowed to dry. Two plants were sprayed with only the diluted solvent-emlsifier solution to serve as checks. Twenty-four hours later, a suspension of conidia of *Colletotrichum lagenarium* in 0.1% polyoxyethylene sorbitan monolaurate was applied to the foliage by means of a DeVilbiss sprayer and the plants placed in a cart moist chamber at 70° F. for 48 hours. On the 18th day after planting, the plants were returned to the greenhouse and allowed to remain for about 7–9 days, at which time the plants were observed for development of disease symptoms, compared with the check plants, and rated for control. The same values for the rating system were used as in Trial 1. The results are shown in Table 2.

Table 2

| Compound of Example No. | Appln. Rate ppm | Cucumber Anthracnose Control Rating |
|---|---|---|
| 2 | 400 | 4.5 |
|  | 100 | 5 |
|  | 25 | 4 |
| 3 | 400 | 3 |
| 4 | 400 | 4 |
| 6 | 400 | 4 |
| 7 | 400 | 4.5 |
|  | 100 | 5 |
|  | 25 | 4 |
| 10 | 400 | 4 |
|  | 100 | 4 |
| 11 | 400 | 4.5 |
|  | 100 | 4 |
| 12 | 400 | 3.5 |
|  | 100 | 3 |

TRIAL 3

The evaluation of the effectiveness of compounds exemplified by the above formula against *Piricularia oryzae*, Race I, the causative organism of rice blast was accomplished in the greenhouse in the following manner.

Round plastic pots, measuring 6.25 cm. in diameter and containing a 50:50 mixture of sand and loam were thickly seeded with rice seed, *Oryzae sativa* L. 'Nato', and placed in the greenhouse. Fourteen days from the day of planting, the test chemicals, compounded as described in Trial 1, were sprayed on all leaf surfaces of the rice plants and allowed to dry. The diluted solvent-emulsifier solution was sprayed on the leaf surfaces of the rice plants in one pot, which served as a check. Within 24 hours, the foliage of each plant was inoculated with an aqueous 0.1% polyoxyethylene sorbitan monolaurate solution of *Piricularia oryzae*, Race I, conidia, applied with a DeVilbiss sprayer, following which all plants were placed in a cart moist chamber at a temperature of 70° F. for a period of 48 hours, and then returned to the greenhouse on day 17 after planting. On about day 22–24 after planting, the plants were examined for symptoms of the disease and the results recorded. The results are given in Table 3, using the same rating system as in Trial 1.

Table 3

| Compound of Example No. | Appln. Rate, ppm. | Rice blast Control Rating |
|---|---|---|
| 2 | 400 | 4 |
|  | 100 | 4 |
|  | 25 | 4 |
| 3 | 400 | 4 |
|  | 100 | 3 |
| 5 | 400 | 3.5 |
|  | 100 | 4 |
| 7 | 400 | 4 |
| 10 | 400 | 4 |
|  | 100 | 4 |

Table 3-continued

| Compound of Example No. | Appln. Rate, ppm. | Rice blast Control Rating |
|---|---|---|
|  | 25 | 3 |
| 11 | 400 | 4 |
|  | 100 | 4 |
| 12 | 400 | 4 |
|  | 100 | 4 |
| 13 | 400 | 4 |
|  | 100 | 4 |
| 14 | 400 | 3.5 |
| 15 | 400 | 4 |
|  | 100 | 4 |
|  | 25 | 2.5 |
| 16 | 400 | 3 |
| 19 | 400 | 3 |
|  | 100 | 3 |
|  | 25 | 3 |
| 22 | 400 | 4 |
|  | 100 | 4 |
|  | 25 | 4 |
|  | 6 | 3 |
| 25 | 400 | 3 |
| 28 | 400 | 3.5 |
|  | 100 | 3 |

TRIAL 4

The evaluation of the effectiveness of compounds exemplified by the above formula against *Venturia inaequalis*, the causative organism of apple scab, was accomplished in the greenhouse in the following manner.

Four pre-germinated apple seeds, variety *Malus sylvestris* 'McIntosh', were planted in 9.5 cm. square plastic pots containing a 50:50 mixture of peat and sterile soil. The seeds were covered with the same mixture. On the 21st day after planting, when the seedlings had reached the 4–6 leaf stage, all leaf surfaces of the seedlings in one pot were sprayed with formulated chemical. One pot of seedlings was used for each test chemical. Within 24 hours after the spraying, all the plants were inoculated with a conidial suspension of the pathogen and the plants were placed for 48 hours in the moist chamber at a temperature of 65° F. On the 24th day after planting, the plants were transferred to the greenhouse, and allowed to remain for 9 days, at which time the plants were observed for development of disease symptoms and rated for control. The same values for the rating system were used as in Trial 1. The results are shown in Table 4.

Table 4

| Compound of Example No. | Appln. Rate, ppm. | Apple Scab Control Rating |
|---|---|---|
| 1 | 400 | 4 |
| 2 | 400 | 3 |
| 3 | 400 | 4.5 |
|  | 100 | 4 |
|  | 25 | 3.5 |
| 4 | 400 | 5 |
|  | 100 | 5 |
|  | 25 | 4.5 |
| 5 | 400 | 5 |
|  | 100 | 5 |
|  | 25 | 4.5 |
|  | 6 | 4 |
| 7 | 400 | 4 |
|  | 100 | 4 |
|  | 25 | 4 |
| 8 | 400 | 3 |
| 9 | 400 | 3 |
| 10 | 400 | 4 |
| 11 | 400 | 5 |
|  | 100 | 4.5 |

Table 4-continued

| Compound of Example No. | Appln. Rate, ppm. | Apple Scab Control Rating |
|---|---|---|
|  | 25 | 4 |
| 12 | 400 | 4 |
| 14 | 400 | 3.5 |
| 15 | 400 | 4 |
| 22 | 400 | 5 |
|  | 100 | 4 |
|  | 25 | 3 |
| 26 | 400 | 3 |
| 28 | 400 | 2.5 |

TRIAL 5

The evaluation of the effectiveness of compounds exemplified by the above formula against *Helminthosporium sativum*, the causative organism of Helminthosporium leaf spot, was accomplished in the greenhouse in the following manner.

Wheat seed, *Triticum aesativum* L. 'Monon', was planted in 6.25 cm. diameter round plastic pots containing sterile greenhouse soil mixture and topped with a sandy soil cover. On the 6th day after planting, when the wheat seedlings were 10–12.5 cm. tall, one pot for each test chemical was sprayed with the formulated test chemical. One pot for each test chemical was soil drenched with an aliquot of 10 ml. of each test solution. Two pots of wheat seedlings were sprayed with water containing the solvent-surfactant system, and two pots of wheat seedlings were soil drenched with 10 ml. of water containing the solvent-surfactant system. These four pots served as checks. The test chemicals were formulated in the same manner as set forth in Trial 1, supra. All plants were left overnight in the treatment room to allow possible systemic movement of the chemical within the plants. Within 24 hours all plants were inoculated with a spore suspension of *Helminthosporium sativum* and then placed for 48 hours in a moist chamber at a temperature of 70° F., after which all the plants were transferred to the greenhouse for disease development. At the end of 4 additional days (13 days after planting) the plants were observed for symptoms of disease incidence. The appearance of the treated plants was compared with that of untreated plants and ratings of the control of the fungus were recorded. The control rating scale used was the same as that set forth in Trial 1. The results are recorded in Table 5, which follows.

Table 5

| Compound of Example No. | Foliar Appln. Rate, ppm. | Soil Appln. Rate kg./ha. | Helminthosporium Control Rating Foliar | Helminthosporium Control Rating Soil |
|---|---|---|---|---|
| 4 | 400 | —* | 3 | —* |
| 11 | 400 | 12.32 | 3 | 1 |
| 13 | 400 | 12.32 | 3 | 1 |
| 15 | 400 | 12.32 | 4.5 | 4 |
|  | 100 | 3.36 | 3 | 3 |
|  | 25 | 0.784 | 3 | 3 |
| 16 | 400 | — | 4 | — |
|  | 100 | — | 4 | — |
|  | 25 | — | 2.5 | — |
| 17 | 400 | 12.32 | 4 | 4 |
| 20 | 400 | 12.32 | 4 | 1 |

*Not tested

TRIAL 6

The evaluation of the effectiveness of compounds exemplified by the above formula against *Verticillium*

*alboatrum*, strain V3H, the causative organism of Verticillium wilt of cotton, was accomplished in the greenhouse in the following manner.

In 227 g. paper cups there was placed 150 g. of pathogen-infested soil. The test chemicals were applied to the soil and incorporated by placing the cups on a roller. A portion of the soil after mixing was poured into a 6.25 cm. diameter round plastic pot. Four 14-day old cotton plants were placed in each pot and the roots covered with the remaining soil. Each test also included two pots not treated with chemical but otherwise handled the same as treatment pots. All the plants were placed in the greenhouse. On day 14 after planting, symptoms of wilt and defoliation were observed and the results recorded. The results are set forth in Table 6, which follows. The rating scale is the same as that employed in the previous trials.

Table 6

| Compound of Example No. | Appln. Rate kg./ha. | Verticillium Control Rating |
|---|---|---|
| 3 | 44.8 | 4.5 |
|   | 22.4 | 1 |
| 4 | 44.8 | 5 |
|   | 22.4 | 5 |
|   | 11.2 | 1 |
| 7 | 44.8 | 4 |
| 8 | 44.8 | 5 |
| 10 | 44.8 | 3 |
|   | 22.4 | 1 |
| 12 | 44.8 | 4.5 |
|   | 22.4 | 1 |
| 28 | 44.8 | 4.5 |
|   | 22.4 | 1 |

TRIAL 7

The evaluation of the effectiveness of compounds exemplified by the above formula against *Botrytis cinerea*, the causative organism of Botrytis of grape, was accomplished in the greenhouse in the following manner.

Sound shape berries were destemmed and surface sterilized in a 1:5 solution of chlorine water (Chlorox) for about 5 minutes, followed by three rinses with deionized water. These berries were then placed in each of 12 compartments constructed in a 35×22×4 cm. pyrex plate. The berries were suspended 1 cm. above the bottom by a wire screen. Finally, the berries were flamed with a Bunsen burner to injure their surface, and thus predispose them to infection. The grape berries were then sprayed with test chemicals, formulated in the same manner as described in Trial 1. In addition, one grape berry was sprayed with the diluted solvent-emulsifier solution. Within 24 hours all of the berries were inoculated by spraying 5 ml. of conidial suspension per plate. To raise the humidity and insure good disease development, a small volume of tap water was added to each plate containing the berries. The pyrex plates were closed by superimposing an identical plate on top and securing the seam between the two plates with masking tape. All plates were incubated for 48 hours at 25° C. On day 3 after the berries were sprayed with test chemical, the berries were observed for symptoms of the disease and the results recorded. The results are given in Table 7, using the same rating system as in Trial 1.

Table 7

| Compound of Example No. | Appln. rate ppm. | Botrytis Control Rating |
|---|---|---|
| 15 | 400 | 4 |
| 16 | 400 | 4 |
| 17 | 400 | 5 |
| 20 | 400 | 4 |

The test results obtained in the trails described above show the novel compounds of this invention possess utility against both airborne and soilborne plant pathogenic fungi.

I claim:

1. A compound of the formula

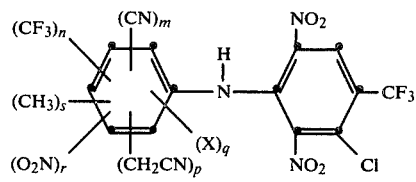

wherein
X is chloro, fluoro, or bromo;
m, p, and s are individually 0 or 1;
n is 0, 1 or 2;
q and r are individually 0, 1, 2, or 3;
the sum of m, n, p, q, r, and s is 1 to 3;
with the proviso that when n is 2, then m, p, q, r, and s are all 0 and the trifluoromethyl groups must be in the 3- and 5-positions; with the further proviso that when s is 1, m and p both are 0 and the sum of n, q, and r is not 0; and with the further proviso that q is 1 only when the sum of m, n, r, and s is not 0.

2. A compound as in claim 1, said compound being 3-chloro-2,6-dinitro-N-(2,4,6-trichlorophenyl)-4-(trifluoromethyl)benzenamine.

3. A compound as in claim 1, said compound being 3-chloro-N-(2,4-dichlorophenyl)-2,6-dinitro-4-(trifluoromethyl)benzenamine.

4. A compound as in claim 1, said compound being 3-chloro-N-(2,6-dichlorophenyl)-2,6-dinitro-4-(trifluoromethyl)benzenamine.

5. A compound as in claim 1, said compound being 3-chloro-N-(3,5-dichlorophenyl)-2,6-dinitro-4-(trifluoromethyl)benzenamine.

6. A compound as in claim 1, said compound being 3-chloro-N-(2,4-dibromophenyl)-2,6-dinitro-4-(trifluoromethyl)benzenamine.

7. A compound as in claim 1, said compound being 3-chloro-2,6-dinitro-N-[4-(trifluoromethyl)phenyl]-4-(trifluoromethyl)benzenamine.

8. A compound as in claim 1, said compound being 3-chloro-N-(2-cyanophenyl)-2,6-dinitro-4-(trifluoromethyl)benzenamine.

9. A compound as in claim 1, said compound being 3-chloro-2,6-dinitro-N-(2,4,5-trichlorophenyl)-4-(trifluoromethyl)benzeneamine.

10. A compound as in claim 1, said compound being 3-chloro-2,6-dinitro-N-(2-chloro-4-nitrophenyl)-4-(trifluoromethyl)benzenamine.

11. A compound as in claim 1, said compound being 3-chloro-2,6-dinitro-N-(2-bromo-4-nitrophenyl)-4-(trifluoromethyl)benzenamine.

12. A compound as in claim 1, said compound being N-[3,5-bis-(trifluoromethyl)phenyl]-3-chloro-2,6-dinitro4-(trifluoromethyl)benzenamine.

13. A composition for controlling plant pathogenic fungi comprising a fungicidally-effective amount of a compound of claim 1 and an agriculturally-acceptable inert diluent.

14. A composition as in claim 13 in combination with a surfactant.

15. A composition as in claim 13 wherein the compound is 3-chloro-2,6-dinitro-N-(2,4,6-trichlorophenyl)-4-(trifluoromethyl)benzenamine.

16. A composition as in claim 13 wherein the compound is 3-chloro-N-(2,6-dichloro-4-nitrophenyl)-2,6-dinitro-4-(trifluoromethyl)benzenamine.

17. A composition as in claim 13 wherein the compound is 3-chloro-N-(2-chloro-4-nitrophenyl)-2,6-dinitro-4-(trifluoromethyl)benzenamine.

18. A composition as in claim 13 wherein the compound is 3-chloro-2,6-dinitro-N-(2,4,5-trichlorophenyl)-4-(trifluoromethyl)benzenamine.

19. A method for controlling plant pathogenic fungi which comprises applying to the loci of the fungi a fungicidally-effective amount of a compound of claim 1.

20. The method of claim 19 wherein the compound is 3-chloro-2,6-dinitro-N-(2,4,6-trichlorophenyl)-4-(trifluoromethyl)benzenamine.

21. The method of claim 19 wherein the compound is 3-chloro-N-(2,6-dichloro-4-nitrophenyl)-2,6-dinitro-4-(trifluoromethyl)benzenamine.

22. The method of claim 19 wherein the compound is 3-chloro-N-(2-chloro-4-nitrophenyl)-2,6-dinitro-4-(trifluoromethyl)benzenamine.

* * * * *

Disclaimer 4,152,460.—*Barry A. Dreikorn*, Indianapolis, Ind. 3-CHLORO-2,6-DINITRO-N-(SUBSTITUTED PHENYL)-4-(TRIFLUOROMETHYL)BENZENAMINES. Patent dated May 1, 1979. Disclaimer filed May 29, 1984, by the assignee, *Eli Lilly and Co.*

Hereby enters this disclaimer to all claims of said patent.

[*Official Gazette December 11, 1984.*]